(12) United States Patent
Cohen et al.

(10) Patent No.: US 12,226,255 B2
(45) Date of Patent: Feb. 18, 2025

(54) SYSTEMS, DEVICES, AND METHODS FOR DISPLAYING MULTIPLE INTRALUMINAL IMAGES IN LUMINAL ASSESSMENT WITH MEDICAL IMAGING

(71) Applicant: PHILIPS IMAGE GUIDED THERAPY CORPORATION, San Diego, CA (US)

(72) Inventors: Asher Cohen, San Francisco, CA (US); Sara Rose Chen, San Diego, CA (US); David Reichel, Andover, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 18/236,994

(22) Filed: Aug. 23, 2023

(65) Prior Publication Data

US 2023/0389891 A1 Dec. 7, 2023

Related U.S. Application Data

(63) Continuation of application No. 16/520,541, filed on Jul. 24, 2019, now abandoned.

(60) Provisional application No. 62/711,927, filed on Jul. 30, 2018.

(51) Int. Cl.
   *A61B 8/08* (2006.01)
   *A61B 8/00* (2006.01)
   *A61B 8/12* (2006.01)

(52) U.S. Cl.
   CPC ............. *A61B 8/0891* (2013.01); *A61B 8/12* (2013.01); *A61B 8/463* (2013.01); *A61B 8/5223* (2013.01); *A61B 8/54* (2013.01)

(58) Field of Classification Search
   CPC ......... A61B 8/0891; A61B 8/12; A61B 8/463; A61B 8/5223; A61B 8/54; A61B 5/1076; G16H 50/30
   See application file for complete search history.

(56) References Cited

U.S. PATENT DOCUMENTS

| 7,846,101 | B2 | 12/2010 | Eberle |
| 2012/0283569 | A1 | 11/2012 | Ciompi |
| 2014/0180035 | A1 | 6/2014 | Anderson |
| 2014/0257087 | A1* | 9/2014 | Elbasiony ............ A61B 5/0084 600/424 |

(Continued)

FOREIGN PATENT DOCUMENTS

JP 2012061086 A 3/2012

*Primary Examiner* — Baisakhi Roy
*Assistant Examiner* — Kaitlyn E Sebastian

(57) ABSTRACT

Systems, devices, and methods for displaying multiple intraluminal images in a luminal assessment are provided. An intraluminal imaging device is provided which is configured to be positioned within a body lumen of a patient and receive imaging data associated with the body lumen. The intraluminal imaging device may be in communication with a controller configured to display two or more transverse images of the body lumen on a single display device. The system may also be configured to automatically measure, display, and compare measurements of features, including misalignment or malapposition of a stent, the diameter and area of the stent at various locations along the stent, as well as the diameter and area of the lumen before the stent is positioned.

18 Claims, 15 Drawing Sheets

(56) References Cited

U.S. PATENT DOCUMENTS

| | | | |
|---|---|---|---|
| 2015/0073279 A1* | 3/2015 | Cai | A61B 8/5207 |
| | | | 600/463 |
| 2016/0015327 A1 | 1/2016 | Merritt | |
| 2016/0206267 A1* | 7/2016 | Shimizu | A61B 8/0891 |
| 2016/0335766 A1* | 11/2016 | Ambwani | G06T 7/11 |
| 2018/0271614 A1* | 9/2018 | Kunio | A61B 90/37 |

* cited by examiner

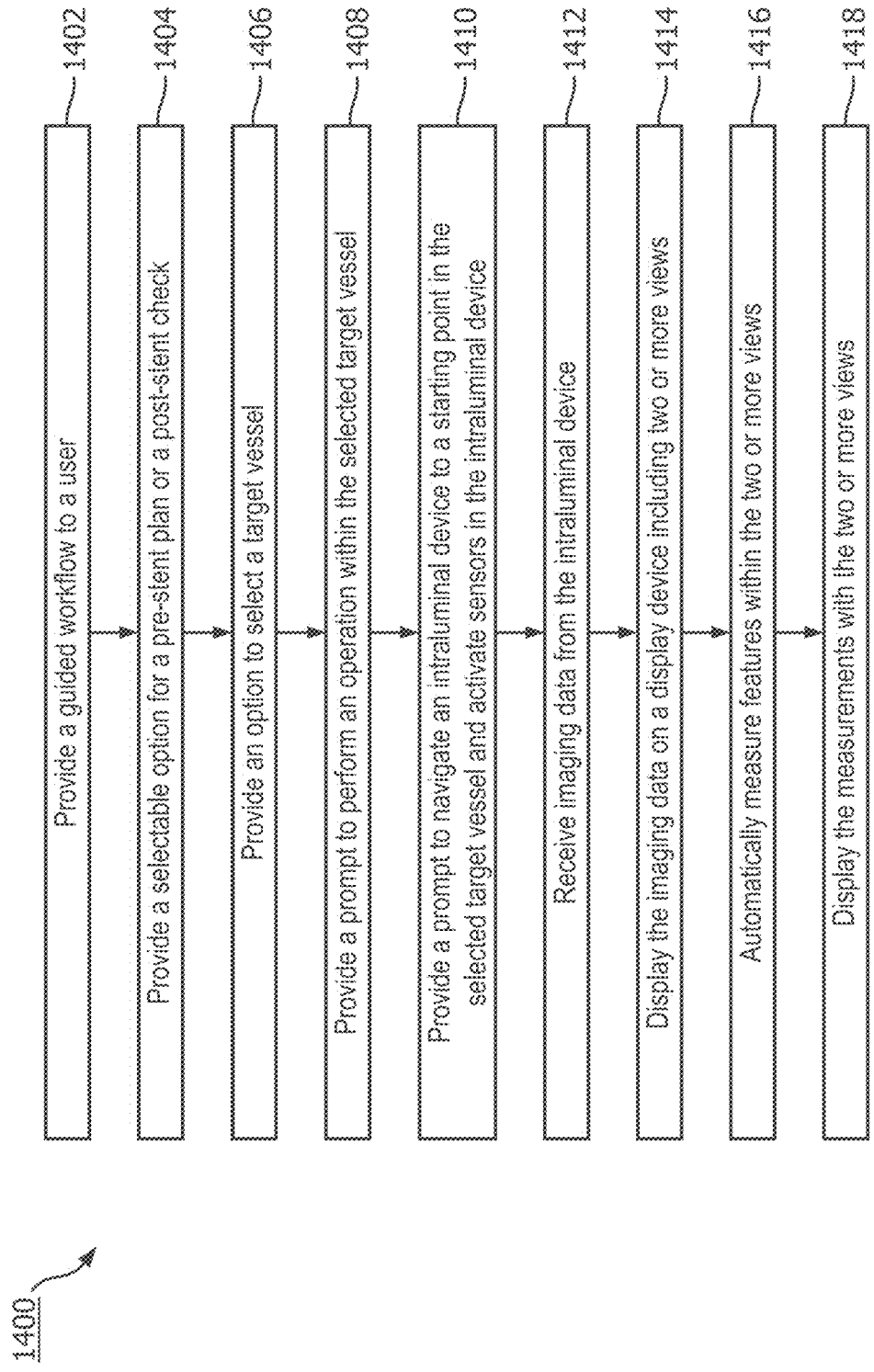

SYSTEMS, DEVICES, AND METHODS FOR DISPLAYING MULTIPLE INTRALUMINAL IMAGES IN LUMINAL ASSESSMENT WITH MEDICAL IMAGING

CROSS-REFERENCE TO PRIOR APPLICATIONS

This application is a continuation of U.S. patent application Ser. No. 16/520,541, filed on Jul. 24, 2019, which claims the benefit of U.S. Provisional Patent Application No. 62/711,927, filed on Jul. 30, 2018. These applications are hereby incorporated by reference herein.

TECHNICAL FIELD

The present disclosure relates generally to intraluminal data associated with a body vessel of a patient, and, in particular, to displaying and comparing multiple intraluminal images (e.g., intravascular ultrasound or IVUS images) on a single screen of a display device.

BACKGROUND

Various types of intraluminal (also referred to as intravascular) imaging systems are used in diagnosing and treating diseases. For example, intravascular ultrasound (IVUS) imaging is widely used in interventional cardiology as a diagnostic tool for visualizing vessels within a body of a patient. This may aid in assessing diseased vessels, such as an arteries and veins within the human body to determine the need for treatment, to optimize treatment, and/or to assess its effectiveness.

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest.

Adoption of intraluminal imaging technology varies around the world and is underutilized in many parts of the world relative to the clinical evidence and benefits it provides. One barrier to the usage of intraluminal imaging is the ease of image interpretation. For example, a user may not be able to understand the meaning of intraluminal images or may not know what to do with this meaning. This barrier has been addressed somewhat with educational courses and tools over the years, but the learning curve is still significant. In particular, intraluminal images are often difficult to interpret and compare in a meaningful way. Furthermore, existing intraluminal images generally involve a large amount of operator input. For example, the operator may be required to examine a large number of images and select a few key images for analysis. Once selected, the operator may also be required to manually tag or measure various features within the images. This process may be time consuming and may lead to inaccuracies in analysis. Thus, deficiencies exist in current intraluminal imaging systems.

SUMMARY

Systems, devices, and methods for displaying multiple intraluminal images are provided. The intraluminal imaging system may include an intraluminal imaging device configured to be positioned within a body lumen (such as a vessel) and a controller configured to receive imaging data from the intraluminal imaging device and display two or more intraluminal images of the body lumen on a single screen of a display device. Each intraluminal image can be associated with a different location along the body lumen. Advantageously, a user is able to view intraluminal images associated with different locations simultaneously. Viewing different locations of, e.g., an occluded blood vessel simultaneously can allow for medical personnel to more easily determine where the ends of a stent should be positioned. Improved efficiency in workflow provides clinical and therapeutic benefits to patients. Aspects of the present disclosure advantageously provide intraluminal images and comparisons that overcome the limitations of existing intraluminal imaging systems.

Embodiments of the present disclosure provide an intraluminal medical imaging system, which may include: an intraluminal imaging device configured to be positioned within a body lumen of a patient and receive imaging data associated with the body lumen; a controller in communication with the intraluminal imaging device, the controller configured to: provide, on a single screen of a display device in communication with the controller, two or more images of the body lumen based on the received imaging data, wherein the two or more images depict different locations within the body lumen; automatically measure an anatomical feature in the two or more images of the body lumen; and display the automatic measurements respectively associated with the two or more images on a display device.

In some embodiments, the controller is further configured to provide, with the display device, a comparison of the two or more images. The controller may be further configured to display, on the single screen of the display device, a longitudinal image of the body lumen. The controller may be further configured to display three transverse images of the body lumen. The longitudinal image may include an indicator correlating the two or more images of the body lumen to their corresponding locations within the body lumen. The controller may be further configured to receive an input from a user corresponding to a location within the body lumen; and display at least one transverse image correlated to the location within the body lumen.

In some embodiments, the three transverse images comprise a first image corresponding with a minimal lumen area (MLA) in the body lumen, a second image corresponding with a location proximal the first image, and a third image corresponding with a location distal the first image. The automatic measurement may be a lumen diameter of the body lumen. The automatic measurement may be one or more of a vessel area, a vessel diameter, a midwall diameter, and a midwall area of the body lumen. The comparison may be of a lumen diameter and a lumen area of the two or more images.

A method of intraluminal medical imaging is also provided, which may include: receiving, with a controller in communication with an intraluminal imaging device positioned within a body lumen of a patient, imaging data associated with the body lumen; providing, on a single screen of a display device in communication with the controller, two or more images of the body lumen based on the received imaging data, wherein the two or more images depict different locations within the body lumen; providing, with the controller, an automatic measurement of a feature on the two or more images of the body lumen; displaying the automatic measurement with the two or more images; and providing, with the display device, a comparison of the two or more images.

The two or more images of the body lumen may be transverse ultrasound images of the body lumen. The method may include displaying, on the single screen of the display device, a longitudinal image of the body lumen. The method may include displaying three transverse images of the body lumen. The longitudinal image may include an indicator correlating the two or more images of the body lumen to their corresponding locations within the body lumen. The method may include receiving an input from a user corresponding to a location within the body lumen; and displaying at least one transverse image correlated to the location within the body lumen.

In some embodiments, the three transverse images comprise a first image corresponding with a minimal lumen area (MLA) in the body lumen, a second image corresponding with a location proximal the first image, and a third image corresponding with a location distal the first image. The automatic measurement may be a lumen diameter of the body lumen. The automatic measurement may be a lumen area of the body lumen. The comparison may be based on calculated values of a lumen diameter and a lumen area of the two or more images.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 14 is a flow diagram of a method of intraluminal imaging according to aspects of the present disclosure.

DETAILED DESCRIPTION

Figure 1:
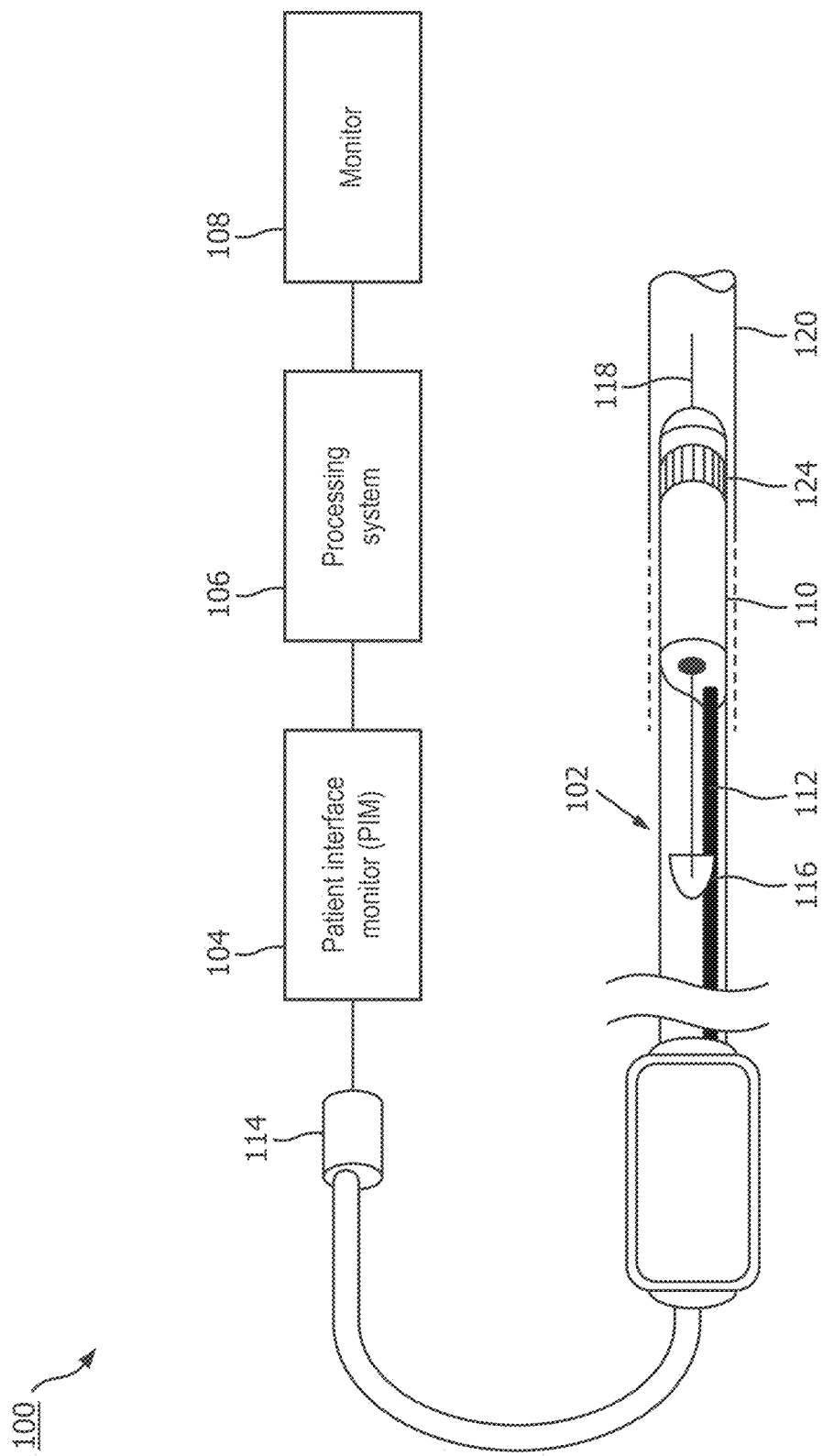
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100, according to aspects of the present disclosure. The intraluminal imaging system 100 may include an intraluminal device 102, a patient interface module (PIM) 104, a console or processing system 106, and a display device or monitor 108. The intraluminal device 102 may be sized and shaped, and/or otherwise structurally arranged or configured to be positioned within a body lumen 120 or vessel of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1.

The devices, systems, and methods described herein can include one or more features described in U.S. Provisional App. No. 62/643,105, filed on an even date herewith, U.S. Provisional App. No. 62/642,847, filed on an even date herewith, U.S. Provisional App. No. 62/712,009, filed on an even date herewith, and U.S. Provisional App. No. 62/643,366, filed on an even date herewith, each of which is hereby incorporated by reference in its entirety.

The intraluminal imaging system 100 (or intraluminal imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 can include an imaging component of any suitable imaging modality, such as optical imaging, optical coherence tomography (OCT), etc. In some embodiments, the device 102 can include any suitable imaging component, including a pressure sensor, a flow sensor, a temperature sensor, an optical fiber, a reflector, a mirror, a prism, an ablation element, a radio frequency (RF) electrode, a conductor, and/or combinations thereof. Generally, the device 102 can include an imaging element to obtain intraluminal data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, instantaneous wave free ratio (iFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, and monitor 108 may be communicatively coupled directly or indirectly to the processing system 106. These elements may be communicatively coupled to the medical processing system 106 via a wired connection such as a standard copper link or a fiber optic link and/or via wireless connections using the Institute of Electrical and Electronics Engineers (IEEE) 802.11 Wi-Fi standards, Ultra Wide-Band (UWB) standards, wireless FireWire, wireless Universal Serial Bus (USB), or another high-speed wireless networking standard. The processing system 106 may be communicatively coupled to one or more data networks, e.g., a Transmission Control Protocol/Internet Protocol (TCP/IP)-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, the intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducers between 1 transducer and 1000 transducers, including values such as 2 transducers, 4 transducers, 36 transducers, 64 transducers, 128 transducers, 500 transducers, 812 transducers, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, select particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or surrounded structures, both natural and man-made. Lumen 120 may be within a body of a patient. Lumen 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as checking on a stent that has been positioned in a lumen. The workflow may be presented to a user as any of the displays or visualizations shown in FIGS. 2-9.

Figure 2:
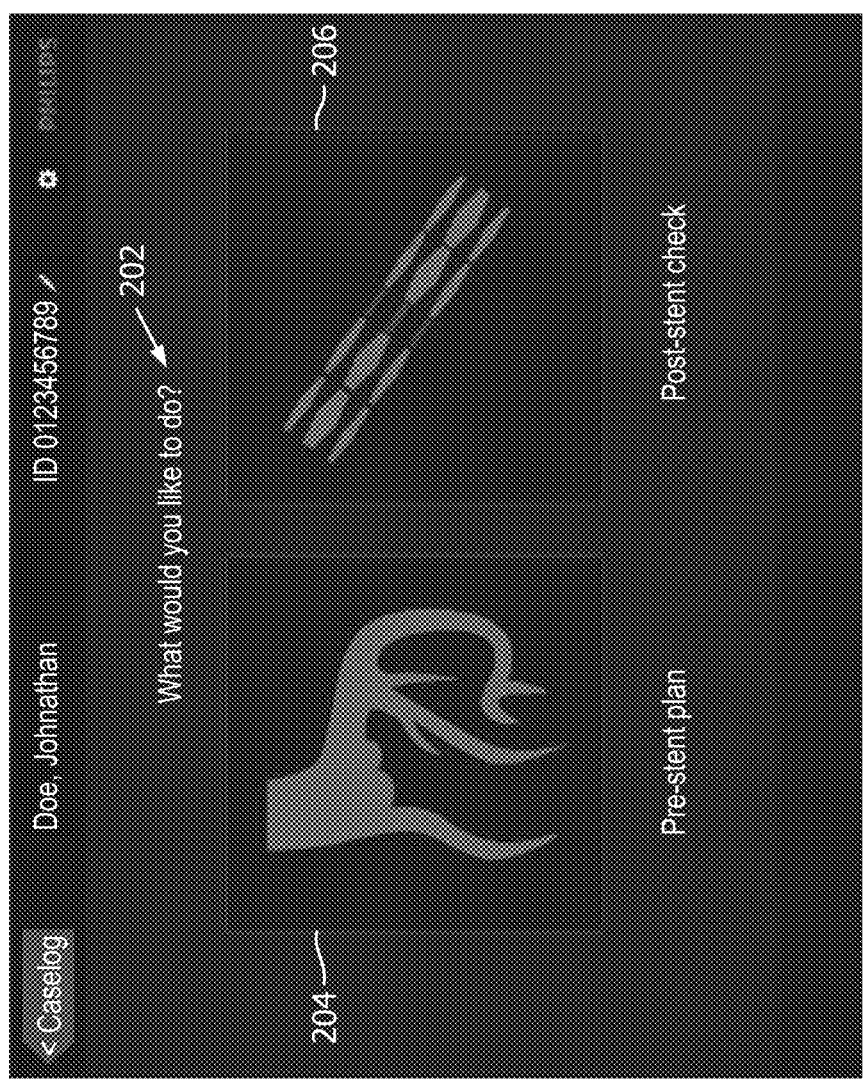
FIG. 2 is an exemplary illustration of a display showing a prompt according to aspects of the present disclosure.

FIG. 2 shows an exemplary display 200 showing a prompt 202 according to aspects of the present disclosure. In some embodiments, the display 200 is displayed on the monitor 108 as shown in FIG. 1. In other embodiments, the display 200 is displayed on a screen of another device, such as PIM 104. The display 200 may be generated by a controller of the intraluminal imaging system 100. In some embodiments, the display 200 is configured to display prompts and instructions as well as other data to an operator. The display 200 may be used to show a complete end-to-end workflow for an intraluminal procedure. This workflow may include a number of prompts and instructions that may guide an operator through a procedure. This may simplify the steps of a procedure and help to avoid operator irregularities.

Figure 3:
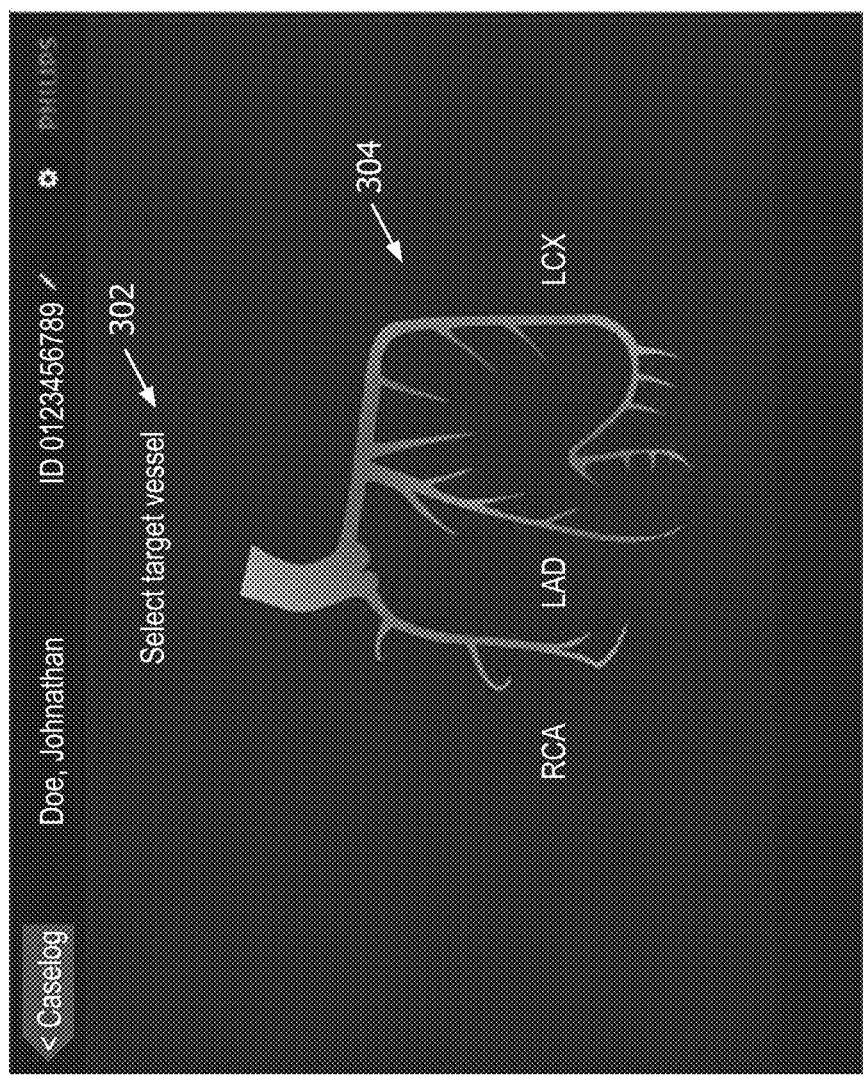
FIG. 3 is an exemplary illustration of a display showing another prompt according to aspects of the present disclosure.

The prompts and instructions may be displayed on the display 200 as selectable options such that an operator may interact with the display 200 to choose options. The selections of the operator may change the display 200 such that information corresponding with the selected options is shown. In the example of FIG. 1, a selectable prompt 202 is displayed on display 200. The prompt includes two selectable options: option 204 corresponds to a pre-stent plan and option 206 corresponds to a post-stent check. The operator may select one of the options 204, 206 which may move the workflow forward, such that other screens are displayed (such as prompt 302 as shown in FIG. 3). The options 204, 206 may include visual representations of the type of procedure. For example, option 204 may include a depiction of vasculature within the heart and option 206 may include a depiction of a stent. In some embodiments, the selection of an option 204, 206 may involve a change in the visual depiction of the option 204, 206. For example, if the pre-stent plan option 204 is selected, the option 204 may appear as shaded or grey in future displays of the display 200. This may help to indicate that this option 204 has previously been selected by an operator. Other types of feedback may be used to indicate selections of options. For example, the selectable options 204, 206 may display blinking areas, highlighted areas, altered colors, shading, altered transparencies, and other visual indicators.

Option 204 may provide a workflow for a pre-stent plan that may include performing an intraluminal procedure (such as a pullback operation) and viewing results. Option 204 may be used to identify areas within a lumen 120 that may benefit from the placement of a stent. Option 206 may provide a workflow for a post-stent check that may include performing an intraluminal procedure (such as a pullback operation) and viewing results of an area within a lumen 120 where a stent has previously been placed. This option 206 may be used to observe the placement and effectiveness of the stent.

FIG. 3 shows an exemplary display 200 showing a prompt 302 according to aspects of the present disclosure. The colors, shading, textures, and other graphical properties of the display 200 may be chosen to highlight specific features. In some embodiments, the prompt 302 may be displayed after either of the options 204, 206 are selected. In other embodiments, the prompt 302 is displayed only after the pre-stent plan option 204 is selected. The prompt 302 may prompt the operator to select a target vessel. In the example of FIG. 3, selecting the target vessel includes selecting a region on a visualization 304 including arteries in the heart. The selectable regions may include the right coronary artery (RCA), left anterior descending (LAD), and left circumflex artery (LCX). The selectable regions may also include various regions of the arteries, as well as other vessels and lumens within other parts of the anatomy of a patient. The appearance of the visualization 304 may be altered when one of the regions is selected by the operator. For example, the selected artery may be outlined, highlighted, or colored with a different color. In some embodiments, the selected artery is outlined in a contrasting color (e.g., blue, red, or another color), shaded, shown with a texture, or otherwise highlighted.

Figure 4:
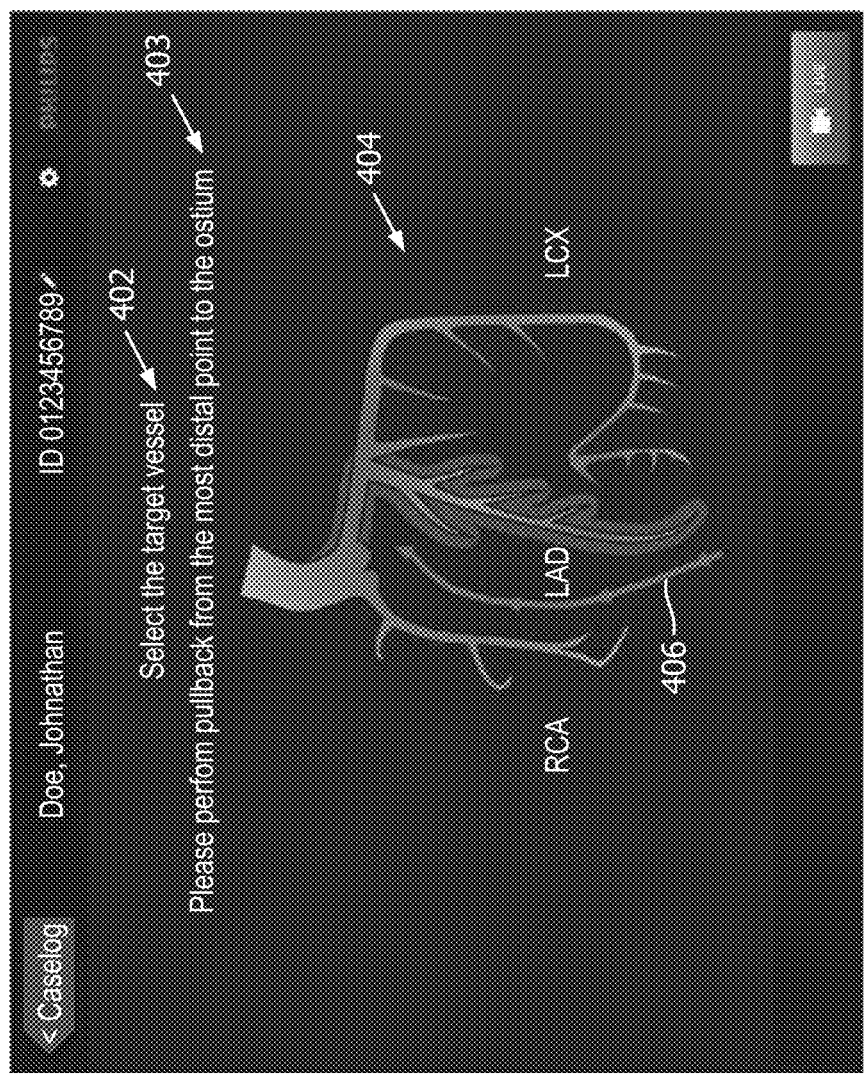
FIG. 4 is an exemplary illustration of a display showing another prompt and instructions according to aspects of the present disclosure.

FIG. 4 shows an exemplary display 200 showing a prompt 402 according to aspects of the present disclosure. The prompt 402 may be displayed after the operator has made a selection on the prompt 302 shown in FIG. 3. In the example of FIG. 4, the LAD artery has been selected by an operator. The prompt 402 shows the outlined image of the LAD along with instructions 403 to perform a pullback procedure from the most distal point on the LAD to the ostium. These instructions 403 may refer to a pullback procedure or other movement of the device 102 within the selected vessel or lumen 120. The instructions 403 may instruct an operator to perform any type of movement of the device 102 within a selected target vessel. For example, the instructions 403 may instruct an operator to push the device 102 a given distance along the selected target vessel. A visualization 404 corresponding to the instructions 403 may also be displayed on the display 200. In the example of FIG. 4, the visualization 404 includes a line 406 with arrows showing the direction in which the pullback procedure should be performed. The visualization 404 may include visual effects such as changing colors or animation. For example, the arrows of the visualization 404 may move in the direction specified by the instructions 403. The instructions 403 and visualization 404 may vary depending on options that were previously selected. For example, if an operator selected the RCA as the target vessel, the visualization 404 of the RCA would be highlighted and a corresponding visualization would be displayed showing a procedure outlined by instructions 403.

In some embodiments, the instructions 403 of the display 200 may vary depending on which option 204, 206 was selected from the prompt 202 shown in FIG. 2. For example, if the post-stent check option 206 was selected, the instructions may read "please perform pullback from the distal point of the stent to the proximal point of the stent." Other instructions may also be included to guide the operator to perform an imaging procedure and acquire imaging data relevant to the selected target vessel and/or stent.

Figure 5:
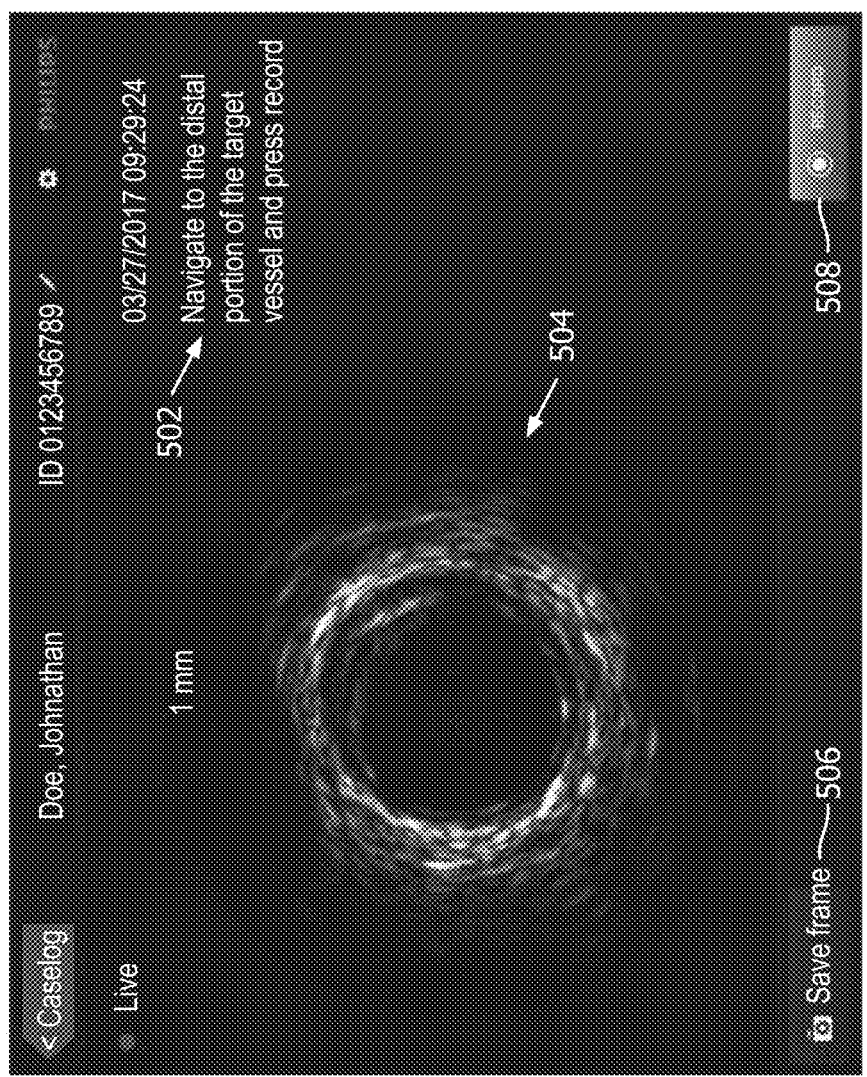
FIG. 5 is an exemplary illustration of a display showing imaging data and instructions according to aspects of the present disclosure.

FIG. 5 shows an exemplary display 300 showing a prompt 502 according to aspects of the present disclosure. The prompt 502 may be displayed after the operator has made a selection on the prompt 402 shown in FIG. 4. In the example of FIG. 5, the LAD artery has been selected by an operator. The prompt 502 may be accompanied by a visualization 504. In some embodiments, the visualization 504 shows imaging data from the device 102 as the device 102 is moved through the selected target vessel. The imaging data may be used as a reference for the operator. In particular, imaging data shown in the visualization 504 may help the operator to know where to begin a procedure. In the example of FIG. 5, the imaging data may show when the device 102 is positioned at a distal end of the LAD artery so that a pullback operation may be performed. The imaging data may also show other reference data such as areas of interest along a lumen 120, branches of the lumen 120, problem areas within the lumen 120, and other features. In some embodiments, when the device 102 is placed at the location specified by the instructions (for example, at a distal portion of an artery), the operator may select the record button 508 to begin a recording of the procedure. The display may also include an option 506 to save specific frames of imaging data before or during a procedure.

Figure 6:
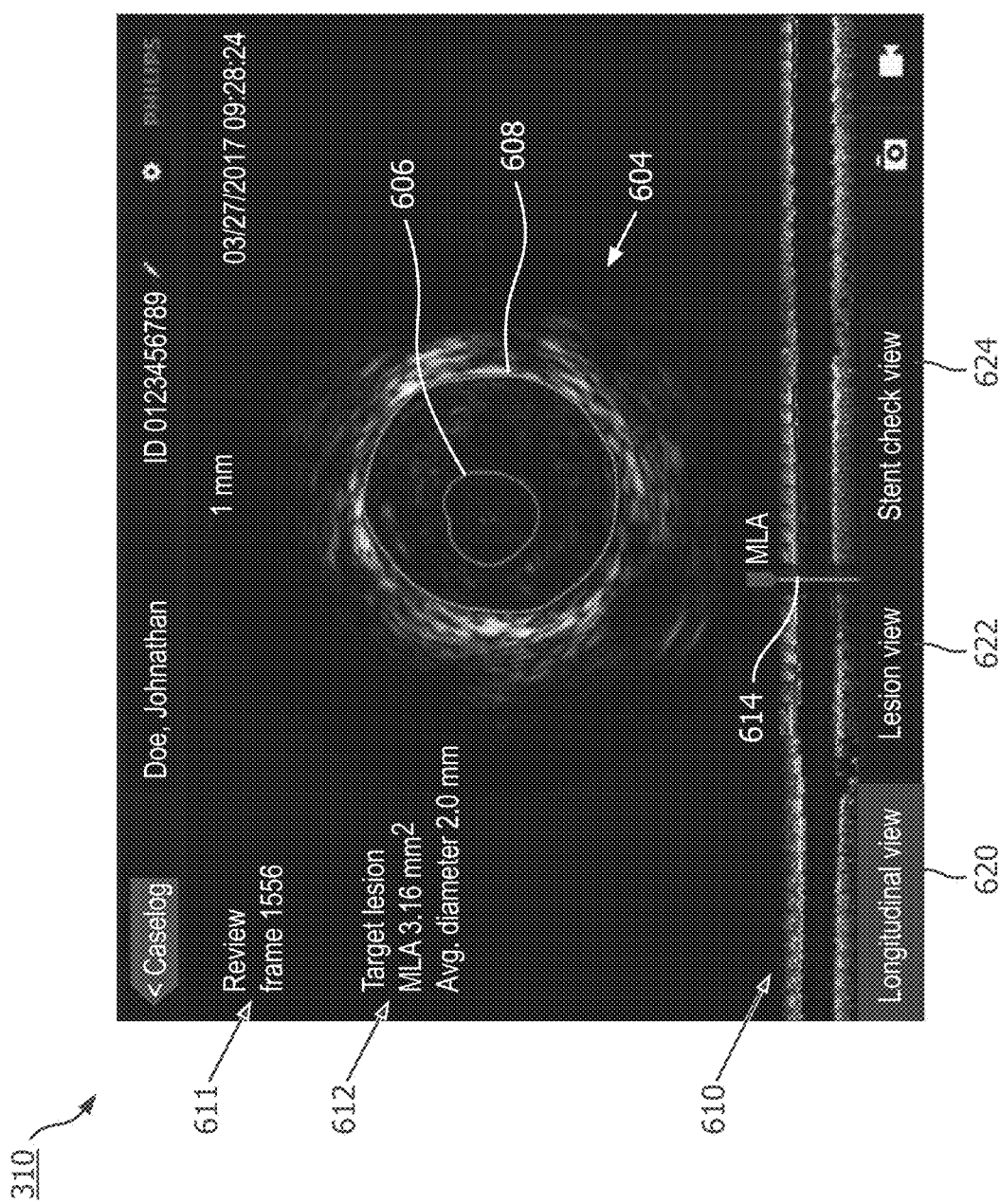
FIG. 6 is an exemplary illustration of a display showing imaging data according to aspects of the present disclosure.
Figure 8:
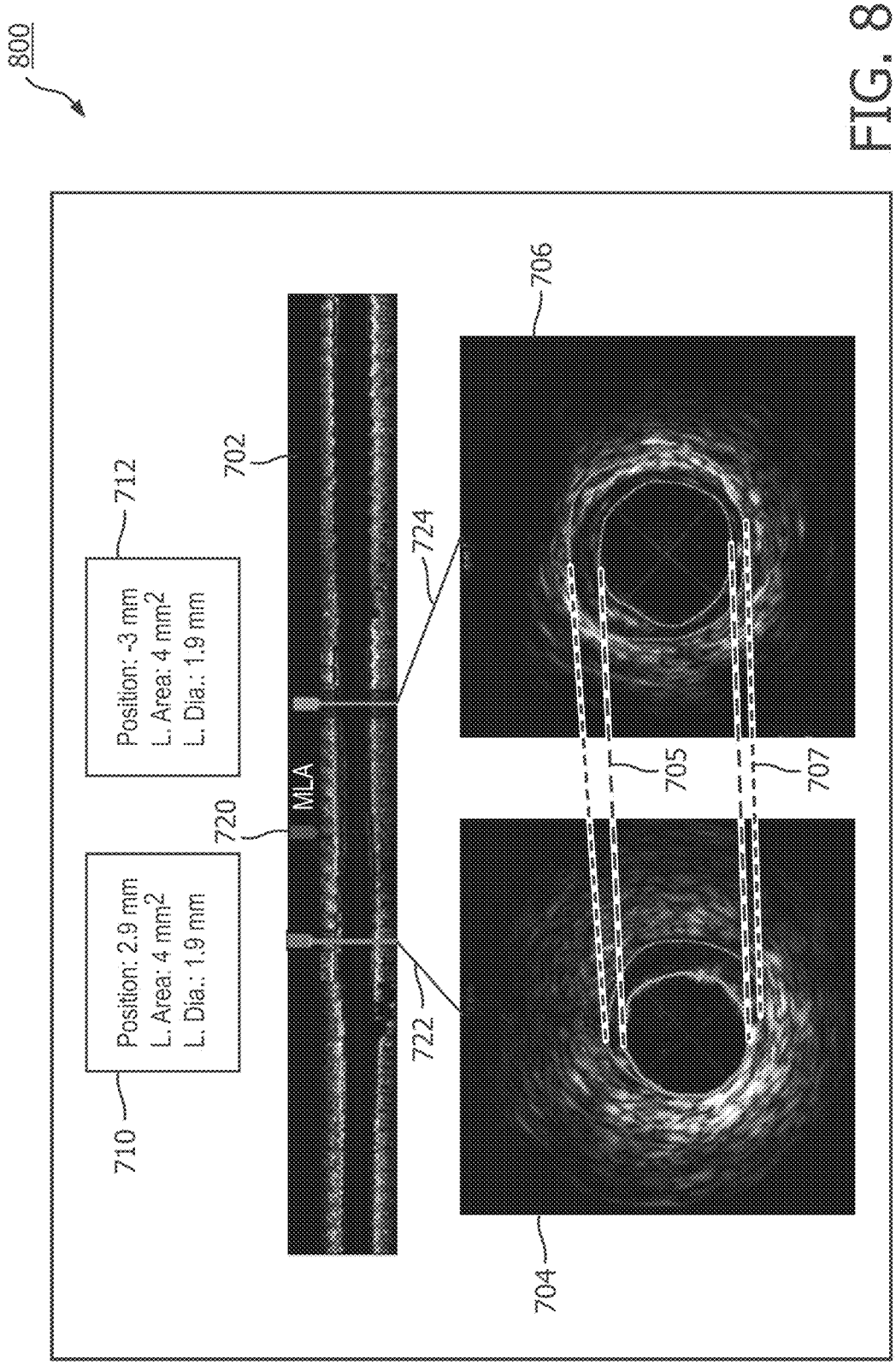
FIG. 8 is an exemplary illustration of another display showing various views of imaging data according to aspects of the present disclosure.
Figure 9:
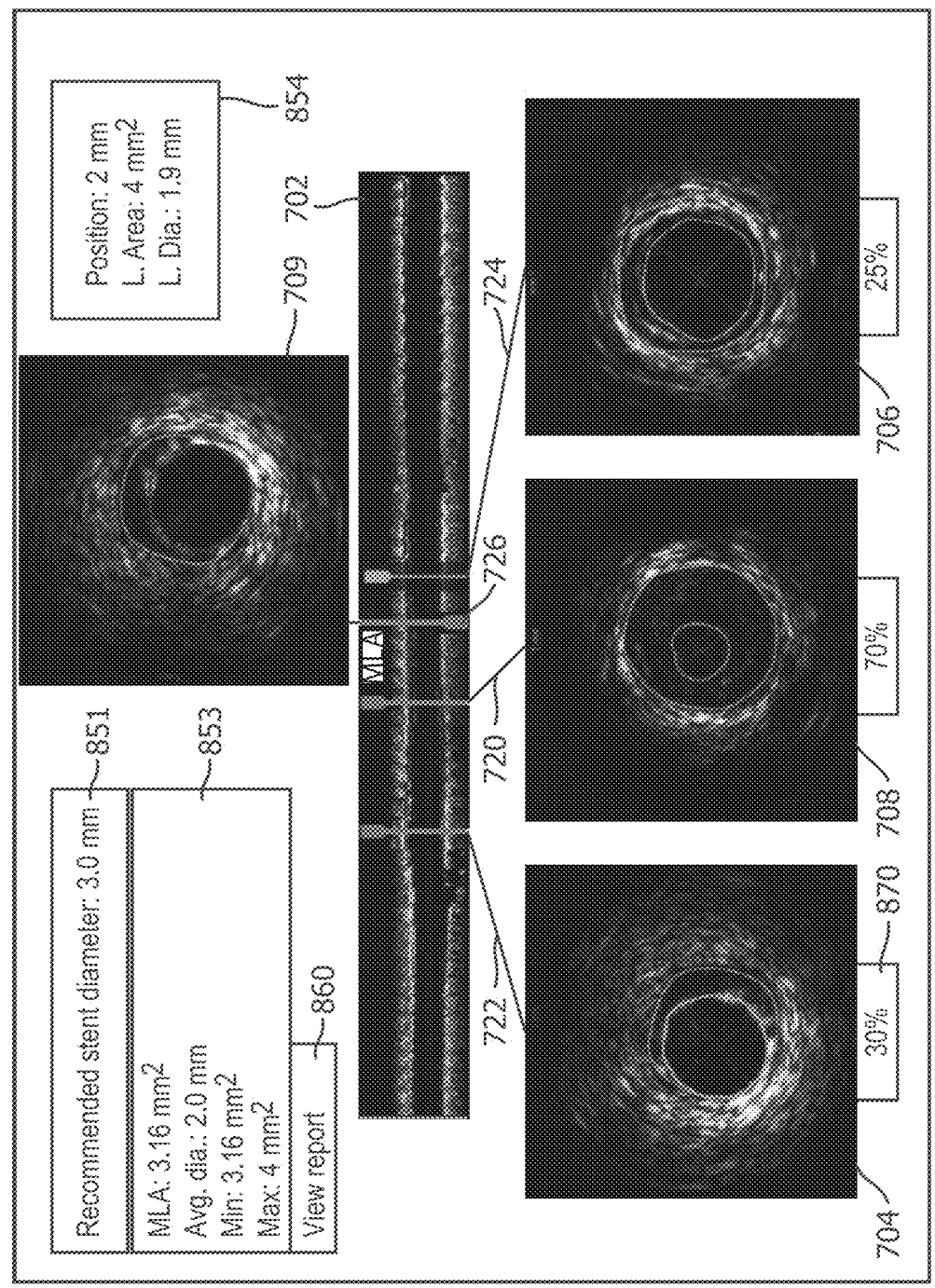
FIG. 9 is an exemplary illustration of another display showing various views of imaging data according to aspects of the present disclosure.
Figure 12A:
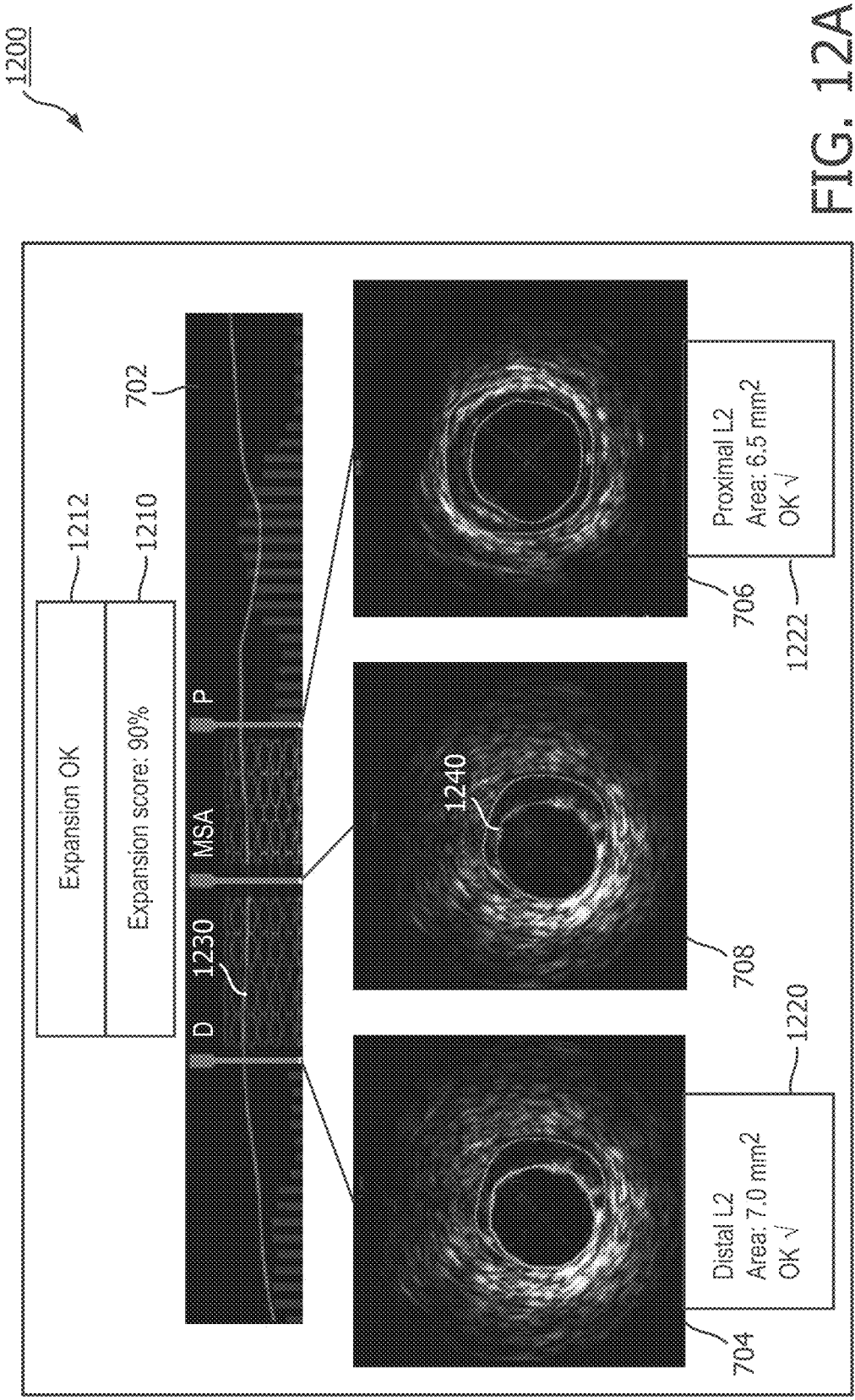
FIG. 12A is an exemplary illustration of a display showing a stent and an expansion score according to aspects of the present disclosure.
Figure 12B:
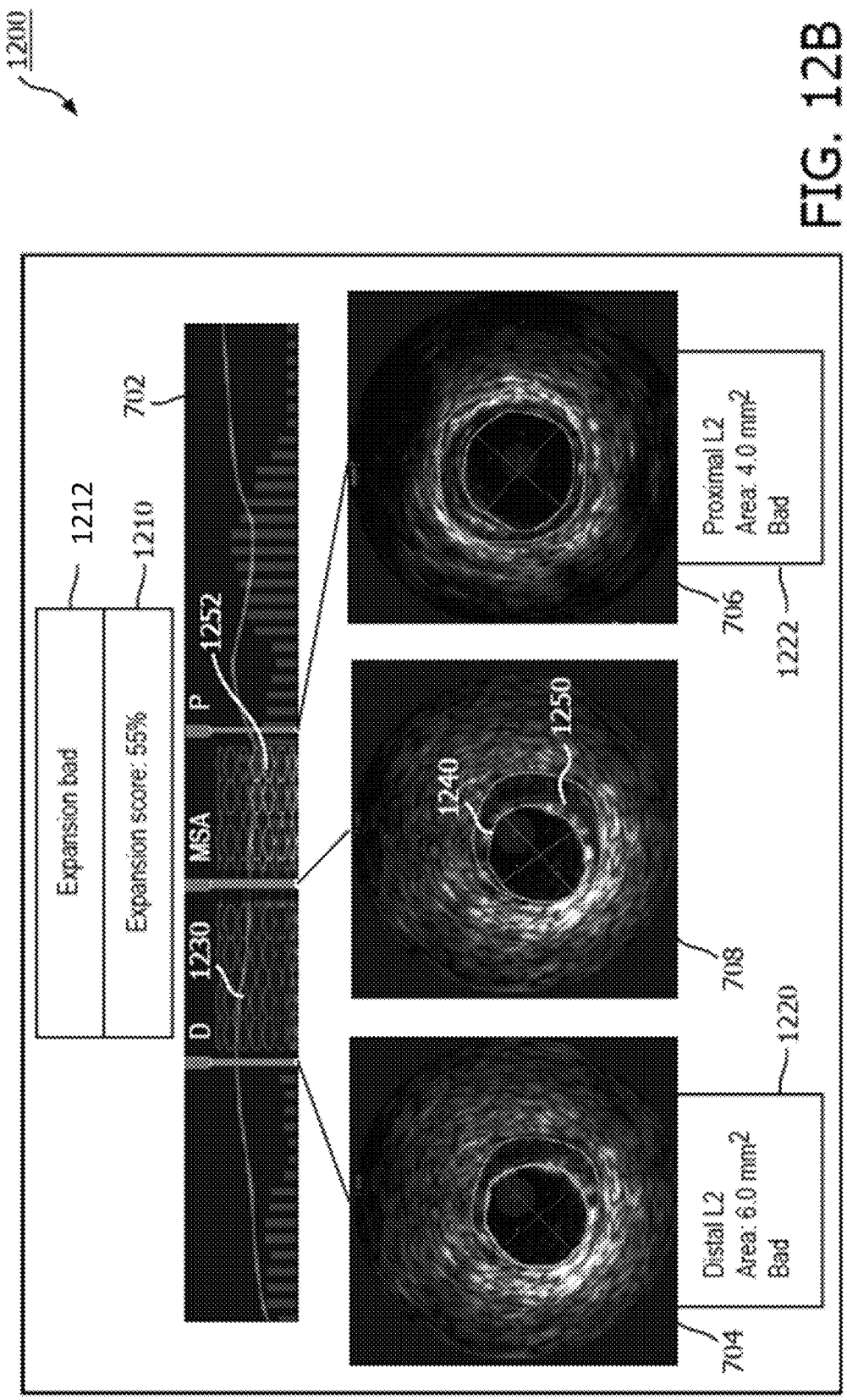
FIG. 12B is an exemplary illustration of another display showing a stent and an expansion score according to aspects of the present disclosure.
Figure 13:
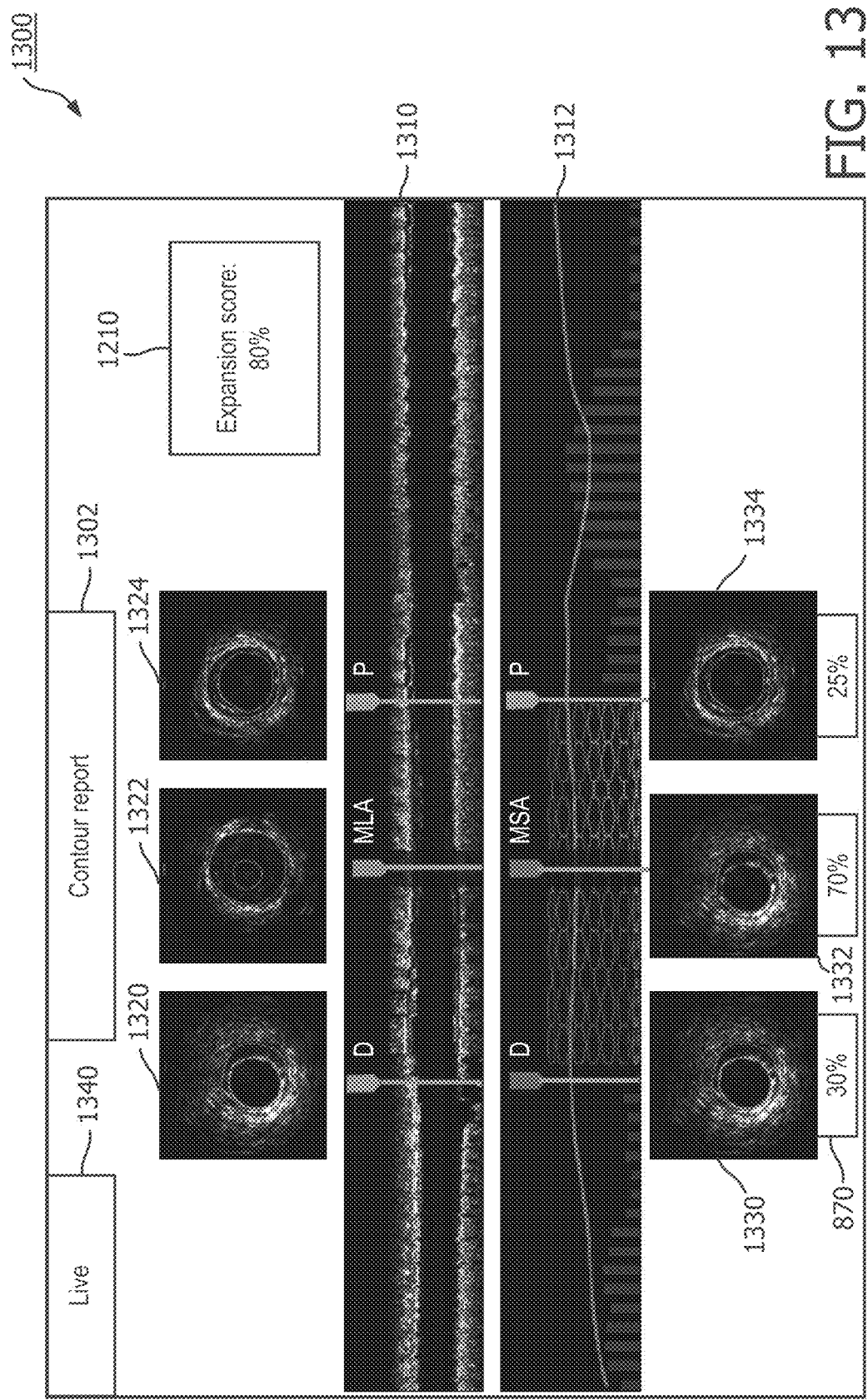
FIG. 13 is an exemplary illustration of a display showing a stent and an expansion score according to aspects of the present disclosure.

FIG. 6 shows an exemplary visualization 310 according to aspects of the present disclosure. The visualization 310 may be displayed on a monitor 108. The visualization 310 may present imaging data acquired by the device 102 during an intraluminal procedure. In some embodiments, the intraluminal procedure is outlined in the instructions shown in FIGS. 3-5. In some embodiments, the visualization 310 includes imaging data corresponding to a lumen 120, such as the selected target vessel. The visualization 310 may include a first view 604 and a second view 610 of the lumen 120. In some embodiments, the first and second views 604, 610 may be oriented 90 degrees apart. In the example of FIG. 6, the first view 604 shows imaging data corresponding to a view straight down the lumen 120 (otherwise discussed as a "transverse view") and the second view 610 shows imaging data corresponding to a longitudinal view of the lumen 120. The views 604, 610 may include corresponding imaging data. The display of the first view 604 and second view 610 is not shown in existing systems, which generally include a single tomographic image. In other embodiments, other views may also be shown, including one or more transverse, cross-sectional, and tomographic images. For example, FIG. 8 shows a longitudinal view and two transverse views of a body lumen, FIG. 9 shows a longitudinal view and four transverse views of a body lumen, FIGS. 12A-B show a longitudinal view and three transverse views of a body lumen, and FIG. 13 shows two longitudinal views and six transverse views of a body lumen. Other combinations of views are also contemplated.

In some embodiments, the visualization 310 may include a selected frame of imaging data (e.g., frame 611) received by the device 102. The operator may be able to select any frame from the imaging data received by the device 102. This may allow the operator to focus on specific areas of interest in the lumen 120.

In some embodiments, measurements are performed automatically on the imaging data with a controller of the intraluminal imaging system 100 as the imaging data is acquired by the device 102. Existing imaging systems typically require an operator to manually select a frame of interest and mark areas for measurement. This may be a time-consuming process, and may introduce user errors, especially in marking areas for measurement. These errors may cause operators to miss important features within the imaging data. The intraluminal imaging system 100 provides automated measurement of features in received imaging data without requiring user interaction. In some embodiments, the system 100 may automatically measure all applicable boundaries in the imaging data (including on a displayed image), including anatomical boundaries (such as lumen boundaries) and stents. Furthermore, the system 100 may automatically identify areas of interest based on the automatic measurements and display these areas of interest, correlated to a longitudinal view or angiographic image of the lumen. This automatic measurement, analysis, and display may provide an easy to understand overview of the lumen of the patient.

In the example of FIG. 6, automatic measurements corresponding to a vessel boundary 608 and a minimum lumen area (MLA) 606 are displayed on the first view 604. The measurements may also include a vessel diameter, a center of the vessel, a vessel boundary 608 area, perimeter, or circumference, and other measurements performed automatically by the controller. These measurements may also be shown on other views. For example, a marker 614 is placed at the MLA in the second view 610 that corresponds with the MLA 606 in the first view 604. This may help an operator to visualize the diameter of vessel boundaries along the lumen 120. The measurements may be displayed in numerical format at box 612 on the visualization 310. Specific portions and views of the visualization 300 may be viewed by an operator by selecting the options 620, 622, and 624.

Figure 7:
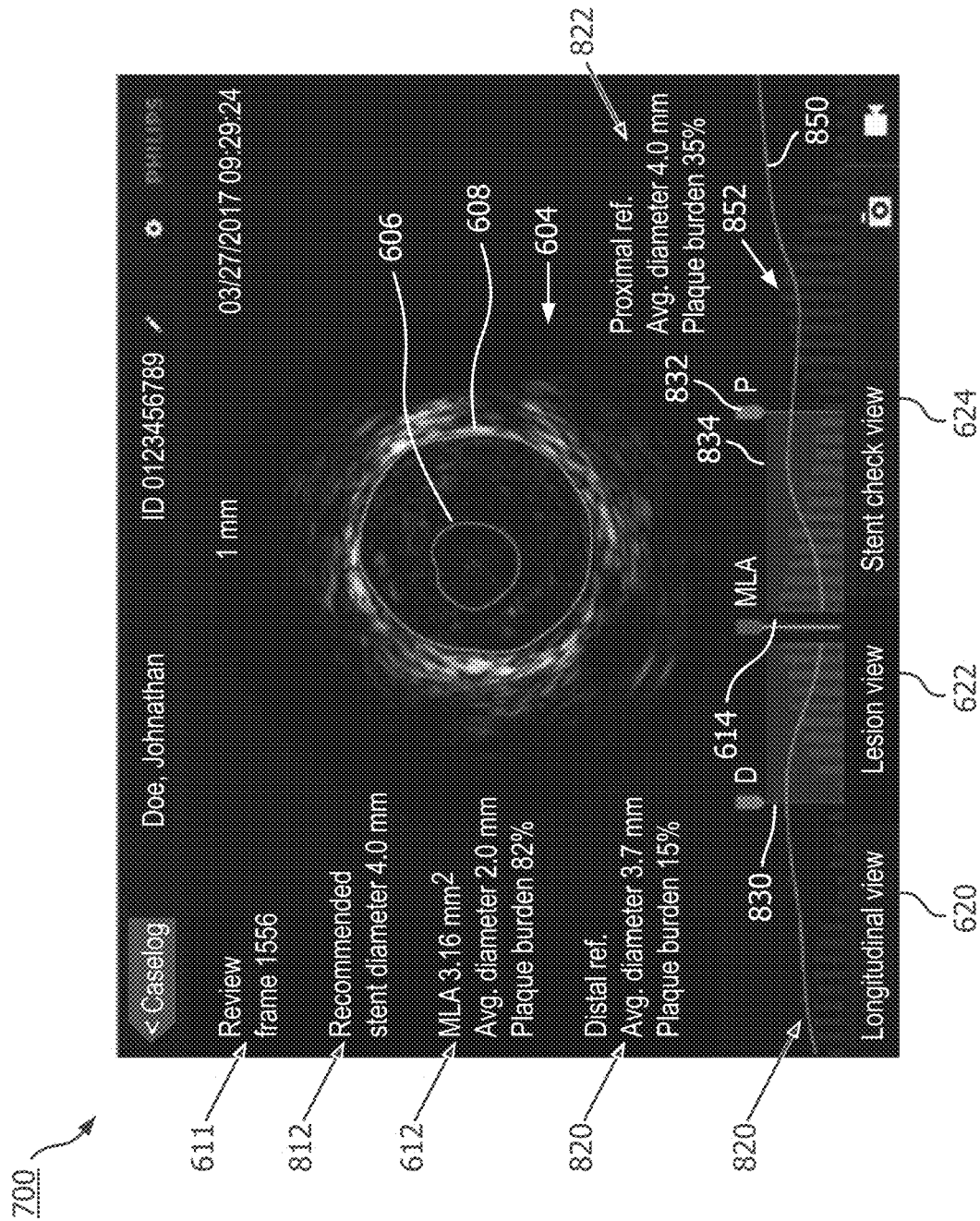
FIG. 7 is an exemplary illustration of a display showing various views of imaging data according to aspects of the present disclosure.

FIG. 7 shows an exemplary visualization 700 showing a lesion view according to aspects of the present disclosure. In some embodiments, visualization 700 corresponds to the pre-stent plan option 204 as shown in FIG. 2. In some embodiments, the visualization 700 may be used to recommend the placement and size of a stent to address a lesion. These recommendations may be made automatically by the system 100 based on the imaging data received by the device 102. In particular, the visualization 700 may be used to visualize a portion of a lumen 120 with a potential "landing zone" 834 for a stent. In some embodiments, the landing zone 834 is an area of interest within the lumen 120 that includes an MLA of a portion of the lumen 120, as marked by marker 614. The landing zone 834 may be shown in profile in view 610 to show the potential placement of the stent within the landing zone 834. A distal end marker 830 and a proximal end marker 832 of the landing zone 834 may define the distal and proximal extent of a potential stent. The distal end marker 830 and proximal end marker 832 may be accompanied with numerical data 820, 822 illustrating the average diameter and plaque burden of the lumen 120 at these locations. In some embodiments, the visualization may also a depiction of the plaque burden 852 along the lumen 120. In some embodiments, the depiction of the plaque burden 852 is automatically measured based on imaging data from the device 102. The visualization 700 may also include a depiction of lumen area 850. As illustrated in FIG. 7, the marker 614 for the MLA may be placed where the plaque burden is the greatest and the area of the lumen is the smallest.

In some embodiments, the visualization 700 includes a recommended stent diameter as shown in text box 812. This diameter may be based on the diameter of the lumen 102 as measured by the system 100.

FIG. 8 shows an exemplary visualization 800 according to aspects of the present disclosure. The visualization 800 may be displayed on a monitor 108. The visualization 800 may include intraluminal images displaying intraluminal imaging data received from an intraluminal device 102 positioned within a body lumen or vessel. In the example of FIG. 8, three intraluminal views are shown: a longitudinal view 702, a first transverse view 704, and a second transverse view 706. The positions of the transverse views 704, 706 may be shown with indicators 722, 724 on the longitudinal view. These indicators 722, 724 may be visually correlated to the transverse views 704, 706 through the use of lines (as shown), as well as corresponding colors, symbols, text, or other visual cues. In some embodiments, the transverse views 704, 706 may be selected manually by a user, such as to mark the boundaries of an area of interest. The longitudinal view 702 may also include a minimum lumen area (MLA) indicator 720 to indicate an MLA within the lumen. The visualization 800 may include one or more text boxes 710, 712. In the example of FIG. 8, the first text box 710 corresponds to the first transverse view 704 and displays data such as a position measurement along the lumen, a lumen area, and a lumen diameter at the transverse view 704. The second text box 712 displays similar data for the second transverse view 706. The text boxes may help to orient the user and provide context for the images shown in the visualization.

In some embodiments, the system 100 may be configured to provide a side-by-side analysis of intraluminal images. For example, the visualization 800 of FIG. 8 includes a comparison between the border measurements of the first transverse view 704 and the second transverse view 706. The size and position of the borders may be compared using lines 705 and 707. In some embodiments, the visualization 800 may include numerical comparison data, such as the difference in measurement between various features within the lumen. An operator may be able to hide or minimize various images in the visualization 800. This side-by-side comparison may help operators to quickly assess differences in viewed images. In some embodiments, the operator may overlay images, such as overlaying the first transverse view over the second transverse view.

FIG. 9 shows an exemplary visualization 900 that may be displayed on a monitor 108. The visualization 900 may include five different views of intraluminal data including a longitudinal view 702 and transverse views 704, 706, 708, and 709. In some embodiments, the transverse view 704 may show a distal end of an area of interest transverse view 706 may show a proximal end of the area of interest, transverse view 708 may show a MLA of the lumen, and transverse view 709 may be manually moved by a user to display any position along the lumen. In some embodiments, the position of each of the transverse views 704, 706, 708, and 709 is shown on the longitudinal view 702, for example by indicators 720, 722, 724, 726. The indicator 726 may be a scrubber that may be moved by a user to view different views along the lumen. In some embodiments, the transverse view 709 includes a highlighted border or other distinguishing feature to allow it to be easily identified by the user. The visualization 900 may include text boxes 851, 853, 854, 860. Text box 854 may show data corresponding to transverse view 709. Text box 853 may show data corresponding to the entire lumen or a portion of the lumen, such as MLA, average diameter, minimum area, maximum area, and other data. Text box 851 may include a recommended stent diameter based on the measurements displayed in text box 853. The view report box 860 may be selected by the user to display a report including the received imaging data, measurements, recommendations, patient information, and other medical data. The visualization 900 may also include a percentage box 870 below the various views 704, 706, 708 to show a percent stenosis of the lumen at the position of the view. For example, the percent stenosis at the MLA may be 70%. This data may help a user to easily compare various regions of the lumen to assess diseased areas and optimize treatment.

Measurements and/or metrics corresponding to the imaging data may be performed automatically by the intravascular imaging system and displayed by the visualization 900. For example, the intravascular imaging system 100 may be used to perform length measurements such as minimum, maximum, average, and mean lengths of features in the imaging data. The effective diameter of features may also be measured. Area measurements of features such as lumens, vessels, plaque, and thrombus may be performed by the intravascular imaging system 100. The measurements may include plaque burden, percent stenosis, percent difference, diameter stenosis, percent diameter stenosis, luminal gain, and luminal gain percentage. Furthermore, features of a stent may also be measured by the intravascular imaging system 100, including overall stent area, minimum stent area, average stent area, stent apposition, expansion, malapposition, and a stent score. The visualization 900 can include numerical values of one or more of these measurements or other graphical representations (e.g., shading, coloring, etc.), including graphical representations overlaid on or displayed separately/spaced from tomographic, longitudinal, and/or angiographic images of a vessel.

Figure 10:
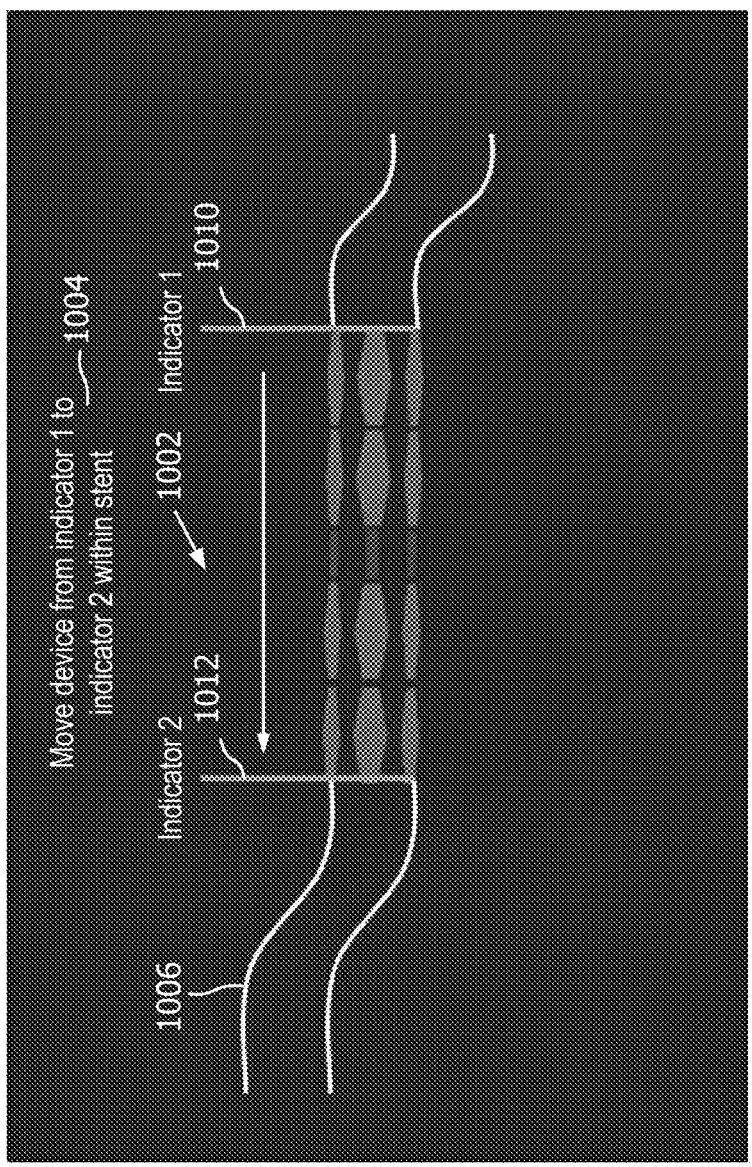
FIG. 10 is an exemplary illustration of a display showing a prompt according to aspects of the present disclosure.

FIG. 10 shows an exemplary display 1000 showing a prompt 1004 according to aspects of the present disclosure. In some embodiments, the display 1000 is shown after the operator has selected the stent check option 206 as shown in FIG. 2. After selecting the prompt, the system may guide the operator through subsequent workflow steps. The operator may then be prompted to move the device 102 through a selected lumen 1006 to collect imaging data based on the stent and surrounding tissue layers in the lumen. The prompt 1004 may instruct the operator with a visualization 1002 showing that the device 102 should be moved from a first indicator 1010 to a second indicator 1012. In some embodiments, the indicators 1010, 1012 are positioned to coincide with proximal and distal ends of the stent. The display 1000 may include an animation showing the correct position and movement of the device 102.

Figure 11:
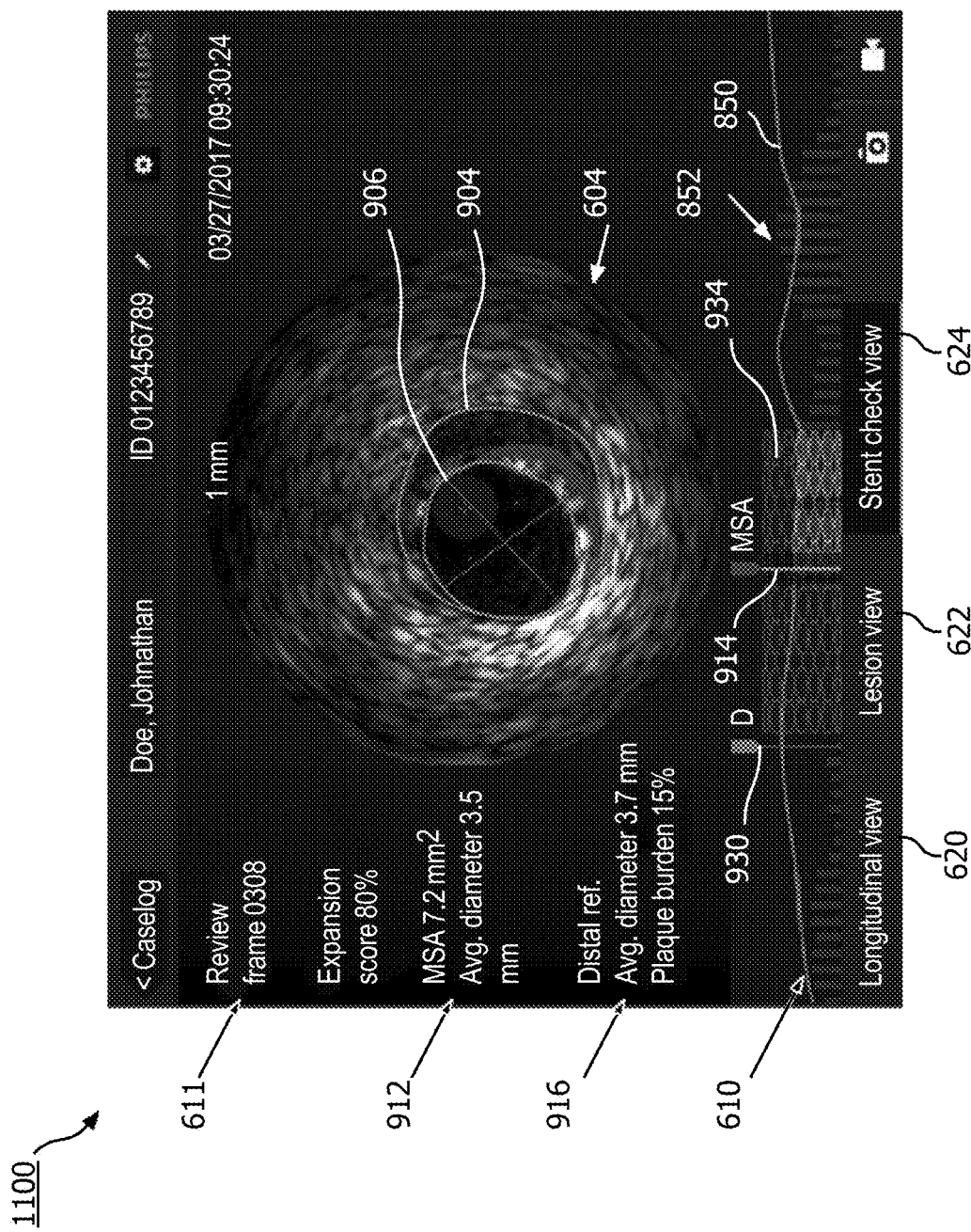
FIG. 11 is an exemplary illustration of a display showing a stent according to aspects of the present disclosure.

FIG. 11 shows an exemplary visualization 1100 showing a stent within a lumen according to aspects of the present disclosure. In some embodiments, the visualization 1100 is shown after the operator has selected the stent check option 204 and has been guided through the subsequent workflow steps. The visualization 1100 may display imaging data gathered from the device 102 during motion within a lumen 120 (such as a pullback procedure) where a stent has been placed, as well as imaging data of surrounding areas of the lumen. Measurements corresponding to the imaging data may be performed automatically. For example, the shape and size of a lumen boundary 904 may be measured and displayed, as well a boundary of the stent 906. As in FIGS. 5-9, the lumen may be visualized in a first view 604 as well as a second view 610. The visualization 1100 may also include measurements of the length of the stent. For example, the visualization 1100 may include a distal reference marker 930 and may include a depiction 934 of the stent. The average diameter and plaque burden at the distal reference marker may be shown in text box 916. The minimum stent area (MSA) may also be automatically measured and displayed in the text box 912 as well as with MSA marker 914.

FIGS. 12A and 12B show an exemplary visualization 1200 showing a lumen with a stent according to aspects of the present disclosure. In some embodiments, the visualization 1200 is shown after the operator follows the prompt 1004 as shown in FIG. 10. The imaging data may be collected by the device 102 as it is moved through the lumen and in particular, through a stent within the lumen. In some embodiments, the system may automatically detect position of the stent and display a visualization of the stent 1230 on the visualization 1200. In the example of FIG. 12A, the visualization shows a longitudinal view 702 is shown on a same screen as transverse views 704, 706, 708. The first transverse view 704 may show a may show a distal reference point on the stent (such as the distal edge of the stent), the second transverse view 706 may show a may show a proximal reference point on the stent (such as the proximal edge of the stent), and the third transverse view 708 may show a MLA within the stent. The transverse views 704, 706, 708 may be visually correlated to the longitudinal view, such as with lines as shown. In other embodiments, the position transverse views 704, 706, 708 may be shown in the transverse with colors, symbols, shapes, text boxes, or other visual indicators.

The diameter and area of the stent in each of the transverse views 704, 706, 708 may be automatically calculated and compared to other imaging data. For example, the calculated area and diameter of the each of the transverse views 704, 706, 708 may be compared to corresponding measurements in a pre-stent procedure. In this way, an operator may be able to check the effectiveness of the placed stent. Misalignment or malapposition of the stent may also be automatically detected and displayed by the system. For example, a malapposition area 1250, 1252 may be shown in both the transverse view 708 and the longitudinal view 702 so that an operator can better visualize the malapposition. The malapposition areas 1250, 1252 may have a different color than other imaging data (such as red) to highlight this feature. In some embodiments, the malapposition areas 1250, 1252 are measured automatically using the imaging data collected by the device 102 during a pullback procedure of the stent. Other aspects of the lumen may also be automatically measured, such a problematic areas due to a bifurcation, previously placed stents, or other complications. These aspects may be accompanied by visual cues such as highlighted areas or symbols and may have associated warnings to alert the operator of their presence.

These comparisons between automatically measured parameters may be used to generate an expansion score 1210 that is displayed alongside the views of the stent and surrounding lumen. In some embodiments, the expansion score is measured as a percentage of change in the lumen after a stent is placed. The expansion score 1210 may be determined automatically with the controller of the system 100 by comparing measurements of the border of the stent 906 to the borders of the lumen. A prompt 1212 may be included in the visualization 1200 showing an interpretation of the expansion score. In the example of FIG. 12A, the expansion score is 90%, which may correspond to a "Expansion OK" prompt. In the example of FIG. 12B, the expansion score is 55%, which may correspond to a "Expansion Bad" prompt. In some embodiments, an expansion over 75, 80, 85, or 90% may correspond to an "OK" prompt, and an expansion under 75, 60, 55, or 50% may correspond to a "Bad" prompt. The prompt 1212 may simplify the expansion to be easily understood by an operator. Data relating to various views, such as transvers views 704 and 706 may be displayed alongside the views 704, 706 in text boxes 1220, 1222.

In some embodiments, an operator may be able visualize possible changes in the stent or lumen of the patient by manually moving aspects of the visualization 1200. For example, the operator may manually drag the border 1240 of the stent to visualize different stenting scenarios, such as placing an additional stent in the lumen.

FIG. 13 shows an exemplary visualization 1300 that may include a contour report 1302 of a procedure. The contour report 1302 may provide a before and after view of a lumen where a stent has been positioned. The visualization 1300 may include a pre-stent longitudinal view 1310 and a post-stent longitudinal view 1312, as well as pre-sent transverse views 1320, 1322, 1324 and post-stent transverse views 1330, 1332, 1334 of the lumen. The transverse views 1320, 1322, 1324, 1330, 1332, 1334 may show distal references, MLA, MSA, and proximal references of the lumen. The diameter and area of each view may be automatically calculated by the system and displayed on the visualization 1300. The comparison of the pre-stent views 1310, 1320, 1322, 1324 and post-stent views 1312, 1330, 1332, 1334 of the lumen may allow the operator to view the effectiveness of a stent procedure. The comparison may be accompanied by data such as expansion percentages 870 at the distal and proximal edges of the stent as well as at the MSA. The overall expansion score 1210 of the procedure may also be displayed which may be generated with the other automatic measurements. The operator may be able to select any of the indicators on the longitudinal views 1310, 1312 and drag the indicators to view imaging data on neighboring frames. The operator may be able to select any of the views 1310, 1312, 1320, 1322, 1324, 1330, 1332, 1334 to enlarge the images and edit the boundaries shown therein. The operator may be able to select the LIVE button 1340 to collect and view additional imaging data, such as data related to a certain area within the lumen.

FIG. 14 is a flow diagram of a method 1400 of proving a guided workflow for an intraluminal imaging procedure to a user. In some embodiments, the steps of the method 1400 may be carried out by the intraluminal imaging system 100 and associated components as shown in FIG. 1. It is understood that the steps of method 1400 may be performed in a different order than shown in FIG. 14, additional steps can be provided before, during, and after the steps, and/or some of the steps described can be replaced or eliminated in other embodiments.

At step 1402, the method 1400 may include providing a guided workflow to a user. The guided workflow may be provided as a series of prompts, instructions, and visualizations that are displayed on a display device, such as monitor 108 as shown in FIG. 1. The guided workflow may help a user to easily and accurately perform each step of an intraluminal imaging procedure. The guided workflow may present different options based on the selections of the user and may include checks of previous steps to ensure that all steps of the procedure have been performed.

At step 1404, the method may include providing a selectable option for a pre-stent plan or a post-stent check. The selectable option may be provided on a display such as display 200 as shown in FIG. 2. The selectable option for the pre-stent plan may include performing an intraluminal imaging procedure to visualize a vessel or lumen before inserting a stent. The selectable option for the post-stent check may include performing an intraluminal imaging procedure to check a stent that has been inserted in a vessel or lumen. Each selectable option may include a number of subsequent steps, as discussed below.

At step 1406, the method 1400 may include providing an option to select a target vessel. This option may be presented visually, such as presenting various vessels on a diagram. In some embodiments, the target vessels are arteries within the heart, such as the RCA, LAD, and LCX. In other embodiments, the target vessels are other lumens within the body. This step 1406 may involve providing feedback to a user, such as indicating which vessel has been selected. The feedback may include highlighting, coloring, shading or otherwise indicating the vessel that has been selected.

At step 1408, the method 1400 may include providing a prompt to perform an operation within the selected target vessel. In some embodiments, this operation includes moving an intraluminal device within the vessel. For example, the operation may be a pullback operation. In other embodiments, the operation may be an operation to push an intraluminal device through a portion of a lumen. The prompt may be presented in text format and may include a visualization of the operation.

At step 1410, the method 1400 may include providing a prompt to navigate an intraluminal device to a starting point in the selected target vessel and activate sensors in the intraluminal device. This prompt may be presented with text as well as images showing where the user should place the intraluminal device. In some embodiments, the prompt of step 1410 depends on the option selected at step 1404. For example, if the user selected the pre-stent plan option at step 1404, the prompt at step 1410 may prompt the user to navigate the intraluminal device from a most distal point of the target vessel to the ostium. If the user selected the post-stent check option at step 1404, the prompt at step 1410 may prompt the user to navigate the intraluminal device from a distal end of the stent to a proximal end of the stent.

At step 1412, the method 1400 may include receiving imaging data from the intraluminal device. This imaging data may help a user to accurately navigate the intraluminal device according to the prompt of step 1410. For example, if the prompt of step 1410 directs the user to navigate the intraluminal device from a distal end of the stent to a proximal end of the stent, the imaging data may show imaging data from the intraluminal device as it is moved to the distal end of the stent. In some embodiments, the imaging data may include IVUS data showing the layers of tissue on the interior of the vessel. In other embodiments, the imaging data includes data from another modality such as OCT. Thus, the imaging data may help the user to accurately perform the operation outlined in the prompt.

At step 1414, the method 1400 may include displaying the imaging data on a display device including two to more views of the lumen. In some embodiments, the imaging data is displayed on a single screen of the monitor 108. The two or more views may include two or more transverse views that are displayed next to each other for comparison, as well as one or more longitudinal views. Any of the views shown in FIGS. 5-9 and 11-13 may be displayed on the display device. The views may show different areas along the vessel, such as a MLA, MSA, and/or proximal and distal reference points. The views may also include pre-stent and post-stent images that may be compared side by side. An operator may be able to select various views for comparison, for example by sliding an indicator along a longitudinal image of the lumen. The operator may also be able to manually edit boundaries of the two or more views.

At step 1416, the method 1400 may include automatically measuring features within the two or more views. These features may include anatomical features such as tissue boundaries, lesions, bifurcations, etc., as well as manmade features such as stents. In some embodiments, the automatic measurements include a diameter and area of the lumen along its length. The automatic measurements may also include one or more of a vessel area, a vessel diameter, a midwall diameter, and a midwall area.

At step 1418, the method 1400 may include displaying the automatic measurements with the two or more views on the display device. The automatic measurements may be displayed with colored borders, symbols, highlighting, text, and other visual features. The measurements may be visually correlated to the views to provide comparison of various data sets to the operator. The automatic measurement may include an expansion score for a stent that is placed within the lumen.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging system, comprising:
   an intraluminal imaging device configured to be positioned within a body lumen of a patient and obtain imaging data associated with the body lumen with a stent; and
   a controller configured for communication with the intraluminal imaging device and a display, wherein the controller is configured to:
      receive the imaging data obtained by the intraluminal imaging device;
      detect a boundary of the stent based on the imaging data;
      detect a boundary of the body lumen based on the imaging data; and
      output, to the display, a screen display comprising:
         a first transverse view of the body lumen based on the imaging data, wherein the first transverse view depicts the stent; and
         a visual indicator within the first transverse view and highlighting a malapposition between the stent and the body lumen, wherein the visual indicator is positioned between the boundary of the stent and the boundary of the body lumen such that the visual indicator is distinct from the boundary of the stent and the boundary of the body lumen.

2. The intraluminal imaging system of claim 1, wherein the controller is configured to:
   automatically detect the malapposition using the imaging data obtained by the intraluminal imaging device during a pullback procedure through the body lumen with of the stent.

3. The intraluminal imaging system of claim 1, wherein the visual indicator is configured to highlight the malapposition with a different color than the other imaging data.

4. The intraluminal imaging system of claim 3, wherein the visual indicator is configured to highlight the malapposition with a red color.

5. The intraluminal imaging system of claim 2,
   wherein the controller is configured to automatically detect a previously placed stent different than the stent, and
   wherein the screen display comprises a visual cue configured to alert a user of the previously placed stent.

6. The intraluminal imaging system of claim 2,
   wherein the controller is configured to automatically detect a bifurcation, and
   wherein the screen display comprises a visual cue configured to alert a user of the bifurcation.

7. A method of intraluminal imaging, comprising:
   receiving imaging data associated with a body lumen with a stent from an intraluminal imaging device;
   detecting a boundary of the stent based on the imaging data;
   detecting a boundary of the body lumen based on the imaging data; and
   outputting, to the display, a screen display comprising:
      a first transverse view of the body lumen based on the imaging data, wherein the first transverse view depicts the stent; and
      a visual indicator within the first transverse view and highlighting a malapposition between the stent and the body lumen, wherein the visual indicator is positioned between the boundary of the stent and the boundary of the body lumen such that the visual indicator is distinct from the boundary of the stent and the boundary of the body lumen.

8. An intravascular imaging system, comprising:
   an intravascular imaging catheter configured to be positioned within a blood vessel of a patient and obtain imaging data associated with the blood vessel with a stent; and
   a controller configured for communication with the intravascular imaging catheter and a display, wherein the controller is configured to:
      receive the imaging data obtained by the intravascular imaging catheter;
      detect a boundary of the stent based on the imaging data;
      detect a boundary of the blood vessel based on the imaging data; and
      output, to the display, a screen display comprising:
         a first transverse view of the blood vessel based on the imaging data, wherein the first transverse view depicts the stent; and
         a visual indicator within the first transverse view and highlighting a malapposition between the stent and the blood vessel, wherein the visual indicator is positioned between the boundary of the stent and the boundary of the blood vessel such that the visual indicator is distinct from the boundary of the stent and the boundary of the blood vessel.

9. The intraluminal imaging system of claim 1, wherein the controller is configured to perform a pre-stent imaging procedure to obtain further imaging data.

10. The intraluminal imaging system of claim 1,
    wherein the screen display comprises at least one of a second transverse view or a third transverse view of the body lumen based on the imaging data,
    wherein the first transverse view, the second transverse view, and the third transverse view are representative of different locations within the body lumen.

11. The intraluminal imaging system of claim 10, wherein at least one of the second transverse view or the third transverse view depicts the stent.

12. The intraluminal imaging system of claim 1, wherein the screen display comprises a longitudinal view of the body lumen based on the imaging data.

13. The intraluminal imaging system of claim 12, wherein the longitudinal view comprises a visualization of the stent.

14. The intraluminal imaging system of claim 13, wherein the screen display comprises a further visual indicator within the longitudinal view and highlighting the malapposition.

15. The intraluminal imaging system of claim 11,
    wherein the stent comprises a distal reference point and a proximal reference point, wherein the second transverse view is representative of the distal reference point and the third transverse view is representative of the proximal reference point.

16. The intraluminal imaging system of claim 15, wherein the distal reference point is a distal edge of the stent and the proximal reference point is a proximal edge of the stent.

17. The intraluminal imaging system of claim 10, wherein the third transverse view is representative of a minimal stent area.

18. The intraluminal imaging system of claim 9, wherein the controller is configured to:
  automatically measure a diameter of the stent and an area of the stent corresponding to the first transverse view; and
  output, to the display, a comparison of the first transverse view,
wherein the comparison is between:
  the diameter of the stent and the area of the stent in the first transverse view; and
  a corresponding diameter of the body lumen and a corresponding area of the body lumen based on the further imaging data from the pre-stent procedure.

\* \* \* \* \*